United States Patent
Ashkar et al.

(10) Patent No.: US 6,673,944 B2
(45) Date of Patent: Jan. 6, 2004

(54) PREPARATION OF WARFARIN SODIUM FROM WARFARIN ACID

(75) Inventors: Michel Ashkar, Western Galilee (IL); Sorin Bercovici, Kiriat Ono (IL); Robert Graff, Randolph, NJ (US)

(73) Assignee: Taro Pharmaceutical Industries, Ltd., Haifa Bay (IL)

( * ) Notice: Subject to any disclaimer, the term of this patent is extended or adjusted under 35 U.S.C. 154(b) by 66 days.

(21) Appl. No.: 09/794,212

(22) Filed: Feb. 28, 2001

(65) Prior Publication Data

US 2002/0120157 A1 Aug. 29, 2002

(51) Int. Cl.$^7$ .......................................... C07D 311/56
(52) U.S. Cl. ........................................ 549/286
(58) Field of Search ........................................ 549/286

(56) References Cited

U.S. PATENT DOCUMENTS

| | | | |
|---|---|---|---|
| 2,427,578 A | 9/1947 | Stahmann et al. | 549/286 |
| 2,752,360 A | 6/1956 | Starr et al. | 549/286 |
| 2,765,321 A | 10/1956 | Schroeder et al. | 549/286 |
| 2,777,859 A | 1/1957 | Link et al. | 549/286 |
| 3,077,481 A | 2/1963 | Schroeder et al. | 549/286 |
| 3,192,232 A | 6/1965 | Schroeder et al. | 549/286 |
| 3,239,529 A | 3/1966 | Preis et al. | 549/286 |
| 3,246,013 A | 4/1966 | Weiner et al. | 549/286 |
| 4,113,744 A | 9/1978 | Badran | 549/286 |
| 4,818,297 A | 4/1989 | Holzmuller et al. | 134/12 |
| 4,826,689 A | 5/1989 | Violanto | 424/489 |
| 5,686,631 A | 11/1997 | Li et al. | 549/285 |
| 5,696,274 A | 12/1997 | Uwaydah et al. | 549/286 |
| 5,856,525 A | 1/1999 | Li et al. | 549/286 |

FOREIGN PATENT DOCUMENTS

| | | |
|---|---|---|
| FR | 1397213 | 12/1963 |
| GB | 1056291 | * 1/1967 |
| WO | WO 97/03062 | 1/1997 |
| WO | WO 97/24347 | 7/1997 |

OTHER PUBLICATIONS

Ohnishi, "Structure–Activity Relationship between the Hydrophobicity of Alkali metal Salts of Warfarin [3–(α–Acetonyl–benzyl)–4–hydroxycoumarin] and the Effectiveness of the Taste Response to These Salts in Mice", Biosci. Biotech. Biochem., 59 (6), 995–1001. 1995.
Ivanov, "New Efficient Catalysts in the Synthesis of Warfarin and Acenocoumarol", Arch. Pharm (Weinheim), 1990, 323, pp. 521–522.
Bush et al, "High yield Synthesis of Warfarin and Its Phenolic Metablites: New Compounds", Journal of Pharmaceutical Science, vol. 72, No. 7, pp. 830–831, Jul. 1983.
Seidman et al, "Studies on 4–Hydroxycoumarins. X. Acylation of 3–(α–Phenyl–β–acetylethyl)–4–hydroxycoumarin", Journal of American Chemical Society, Nov. 1950, pp. 5193–5195.
Ikawa et al, "Studies on 4–Hydroxycoumarins. V. The Condensation of α, β–Unsaturated Ketones with 4–Hydroxycoumarin", Journal of American Chemical Society, 1944, pp. 902–906.
"Warfarin Sodium", Pharmaceutical Manufacturing Encyclopedia, 2$^{nd}$ Ed., vol. 2, 1988, pp. 1590–1591.
Hiskey et al, "Clathrates of Sodium Warfarin" Journal of Pharmaceutical Science, 1965, pp. 1298–1302.
The Merck Index, 12$^{th}$ Edition, 10174. "Warfarin", pp. 1715 (1996).
Kleemann & Engel, et al. "Pharmaceutical Substances" 3$^{rd}$ Ed (English), p. 2010 (1999).
Demir, Ayhan S. et al, Enantioselective Synthesis of 4–Hydroxy–3–(3–Oxo–1–Phenyl Butyl)–2H–1–Benzopyran–2–One (Warfarin), Turk. J. Chem, 1996, pp. 139–145.
Joshi, C.G., et al., Studies in the Synthesis of Warfarin [3–(Acetonylbenzyl)–4–hydroxycoumarin] Indian J. Technol., 1972, pp. 461–462.
Finn, Sidney Louis, Thermogravimetric Analysis of Sodium Warfarin Isopropanol Clathrate (8:4:0), Diss. Abstr. Int. B 1978, 38 (12, Pt. 1), 5951.
Robinson, Andrea, et al., The First Practical Asymmetric Synthesis of R and S–Warfarin, Tetrahedron Lett., 1996, pp. 8321–8324.
Gao, Danchen, et al., Use of Solution Calorimetry to Determine the Extent of Crystallinity of Drugs and Excipients, International Journal of Pharmaceutics 151, 1997, pp. 183–192.
Gao, Danchen, Physical Chemical Stability of Warfarin Sodium, AAPS Pharmaci 2001; pp. 1–8.
Ozcan, Eyup, et al., Factors Affecting the Reaction Efficiency in Warfarin Synthesis, Marmara Univ. Fen Bilimleri Derg., 1989, pp. 155–167 (Article and citation attached).
Yang, Tsang, et al., Synthesis of Anticoagulants, Dicumarol and Warfarin, T'ai–wan K'o Hseu, 1984, pp. 1–7 (Citation only attached).
Manolov, I., et al., Synthesis and Antimetastic Properties of 4–hydroxy–3(3–oxo–1–phenylbutyl)–2H–1–benzopyran–2–one (Warfarin), Farmatsiya (Sofia), 1990, pp. 1–6 (English abstract).
Xu, X.Y., Identification of Principal Components of Clathrate and Complex with Infrared Spectral Subtraction Method, Chinese Journal of Pharmaceutical Analysis (China), V. 17 (Mar. 1997), pp. 87–89 (English abstract).

* cited by examiner

Primary Examiner—Charanjit S. Aulakh
(74) Attorney, Agent, or Firm—Venable; Michael A. Gollin; Keith G. Haddaway

(57) ABSTRACT

The invention provides a method for the direct preparation of pure warfarin sodium from warfarin acid. The reaction is conducted in a polar organic solvent, preferably ethanol, using a volatilizable base, preferably sodium bicarbonate or sodium carbonate, at low temperature. Drying the final product is accomplished at low temperature to avoid decomposition of the final warfarin sodium product.

27 Claims, No Drawings

PREPARATION OF WARFARIN SODIUM FROM WARFARIN ACID

BACKGROUND OF THE INVENTION

1. Field of the Invention

This invention relates to the preparation of warfarin sodium. Specifically, the invention relates to the direct preparation of pure warfarin sodium from warfarin acid at low temperature without decomposition using a polar organic solvent and an inorganic base.

2. Background

Warfarin sodium, known by the chemical name 4-hydroxy-3-(3-oxo-1-phenylbutyl)-2H-1-benzopyran-2-one sodium salt, is a well established, widely used oral anticoagulant and rodenticide. See, for example, U.S. Pat. No. 4,113,744 issued Sep. 12, 1978.) Warfarin sodium and its 2-ropanol clathrate are marketed under various commercial names like Coumadin; Marevan; Prothromadin; Tintorane; Warfarin sodium; Warfilone; Waran.

According to U.S. Pat. No. 3,192,232 to Schroeder and Link, warfarin sodium prepared by existing methods often has as undesirable slight yellow color. (See also, U.S. Pat. No. 3,077,481). Specifically, U.S. Pat. No. 3,192,232 describes aprocess for preparing warfarin sodium and warfarin potassium salts by reacting a slurry or warfarin acid in acetone-water with less than an equivalent of sodium hydroxide or potassium hydroxide in water at room temperature. The solution of the crude salt is purified by stirring with active charcoal and isolating of the salt by evaporation to dryness, spray drying, or drum drying.

U.S. Pat. No. 3,246,013 also emphasizes the difficulties encountered with the preparation of a high purity warfarin sodium. This patent discloses that the removal of the 2-propanol solvent from warfarin sodium 2-propanol clathrate cannot be achieved even with heating at 100° C. over $P_2O_5$ for 3–5 hours in vacuum (0.1 mm Hg). U.S. Pat. No. 3,077,481 further discloses that heating the clathrate at higher temperatures (145° C.) in air at reduced pressure for prolonged time periods (24 hours) results in undesirable decomposition. Also, heating at still higher temperatures (230° C.), while successfully removing 2-propanol from the clathrate, results in rapid decomposition.

U.S. Pat. No. 2,765,321 to Schroeder et al. describes a process of preparing crystalline warfarin sodium by reacting an aqueous sodium hydroxide solution with an excess of warfarin acid, followed by removal of the excess acid by addition of ethanol and filtration. Pure warfarin sodium is obtained only after a salting out procedure using lithium chloride addition into the ethanol-water solution of the warfarin sodium salt, cooling and recovering the precipitated warfarin sodium by filtration.

U.S. Pat. No. 2,777,859 to Link et al. describes a process of preparing an aqueous solution of warfarin alkali metal derivatives by adding an aqueous alkali metal hydroxide to an excess of water wet warfarin acid, warming and removing the excess of warfarin acid by filtration.

Ohnishi et al. have described a method for preparing warfarin alkali metal salts by dissolving warfarin acid in an aqueous solution containing an equivalent amount of the respective alkali metal hydroxide (lithium, sodium, potassium, rubidium and cesium). *Biosci. Biotech. Biochem.* 1995, 59(6), 995–1006 (cf. CA 123: 105246 (1996)) The respective salts are isolated by lyophilization.

In a recent patent, WO 97/24347 (published Jul. 10, 1997), Uwaydah et al. describe a comprehensive process for warfarin alkali salts (sodium and potassium) and clathrate preparation starting from 2-hydroxyacetophenone and a carbonate ester. The hydroxycoumarin thus obtained is further reacted with benzalacetone in the presence of a phase transfer catalyst to give warfarin acid. The latter intermediate is further reacted with sodium or potassium hydroxide or the carbonate, or preferably using sodium or potassium methoxide or ethoxide in anhydrous ethanol or 2-propanol to ultimately yield the desired product.

It is readily apparent that there is a great deal of interest in this field, and a number of synthetic routes for the preparation of warfarin sodium exist. However, existing procedures for the preparation of warfarin sodium have been hampered by several difficulties, notably:

The good solubility of warfarin sodium in most common polar solvents makes isolation difficult. This is further hampered by the immediate conversion of warfarin sodium to warfarin sodium 2-propanol clathrate when 2-propanol is used as a solvent;

Warfarin sodium tends to decompose in the presence of water and excess alkalinity, particularly as the temperature is increased; and The production of dry free-flowing crystals is difficult.

Thus, the need remains for an economical, industrially feasible procedure to produce a high quality, pharmacopeial grade of warfarin sodium.

SUMMARY OF THE INVENTION

In summary, the invention is a method for producing warfarin sodium from warfarin acid in a direct, efficient, and industrially feasible manner. The method involves reacting warfarin acid with a volatalizable inorganic base, preferably sodium carbonate or sodium bicarbonate, in a stabilizing substantially anhydrous polar organic solvent such as ethanol at low temperature. Further purification and isolation is also conducted at moderate temperatures.

This invention solves a problem in the prior art where gel formation accompanies evaporation of the solvent during the preparation of warfarin sodium. In the present invention, gel formation is avoided.

The invention provides advantages not previously appreciated by providing a method for producing pure warfarin sodium wherein the reaction and filtration are conducted at ambient temperature. Furthermore, azeotropic distillation is eliminated entirely.

The invention offers an unforeseen advantage by conducting the final drying in conventional equipment using hot water or low pressure steam as a heating source. The invention is particularly advantageous in that warfarin sodium is not exposed to temperatures in excess of 100° C. which has been found to cause unfavorable decomposition.

This invention is in a crowded and mature art, but achieves the objective of a simple rapid production of warfarin sodium in an efficient, industrially feasible manner without cumbersome purification steps.

The invention differs from the prior art in modifications which were not previously known or suggested by using absolute ethanol as solvent and conducting the reaction and purification steps at low temperatures.

Further objectives and advantages will become apparent from a consideration of the description and examples.

DETAILED DESCRIPTION OF THE PREFERRED EMBODIMENTS

In describing preferred embodiments of the present invention, specific terminology is employed for the sake of clarity. However, the invention is not intended to be limited to the specific terminology so selected. All references cited herein are incorporated by reference as if each had been individually incorporated by reference.

The present invention arises out of a need for a synthesis of warfarin sodium at low temperature. It was found that decomposition of the warfarin sodium occurs when produced by methods requiring elevated temperatures. Furthermore, in the presence of strong bases such as sodium hydroxide and sodium alkoxides normally used for the preparation of warfarin sodium, the warfarin sodium product decomposes, especially at elevated temperatures.

During development of the present invention, the following general parameters known in the art and described in the U.S. and British Pharmacopoeia were continually monitored, investigated and optimized:

(a) Stability of warfarin sodium and warfarin acid in different solvents and at different temperatures as measured by impurity test;

(b) Sensitivity of the reaction to pH control using various solvents, temperatures and bases as measured by pH test;

(c) Stability of warfarin sodium as a function of temperature and reaction time in the presence of excess base using the phenolic ketone test;

(d) Reaction times required when using solvents of differing polarities and using varying ratios of base;

(e) Crystallization of warfarin sodium from mixed solvents or by solvent evaporation; and (f) Water content of the warfarin sodium product.

As a result of these considerations, the inventors focused on developing a process of reacting warfarin acid with (a) weaker bases in (b) substantially anhydrous polar organic solvents to (c) directly produce pure warfarin sodium. It was found that the use of a volatilizable base is particularly preferred. A "volatilizable base" refers to a base having a conjugate acid which is either gaseous or which decomposes to water and/or a gas upon neutralization. Examples of volatilizable bases include carbonates and bicarbonates which, upon neutralization, yield carbonic acid that subsequently decomposes into gaseous carbon dioxide and water. It should be recognized that, when specific reference to sodium carbonate or sodium bicarbonate is made herein, other volatilizable bases may be similarly used.

It was recognized through this work that the decomposition of warfarin sodium during reaction could be avoided by using sodium carbonate or sodium bicarbonate as the volatilizable base and absolute ethanol as solvent. This combination surprisingly allows for the reaction to occur at low temperatures preferably of <50° C., and more preferably at temperatures ranging from about 25° C. to about 35° C. The pH is controlled during work-up by adding small amounts of acids, including warfarin acid. In addition, it was found that, after initial solvent removal and drying in a vacuum oven, the preliminarily isolated warfarin sodium powder is preferably ground to a powder prior to final drying. This allows for the complete drying of the product at relatively low temperatures, preferably less than 70° C., yielding a free flowing powder free of ethanol with excellent yields.

The basic steps involved in preparing warfarin sodium according to the invention are reacting warfarin acid with a volatalizable base, preferably from sodium carbonate and sodium bicarbonate, in a polar organic solvent, preferably absolute ethanol, removing insoluble salts by filtration, and adjusting the pH to a value of from about 7.8 to about 8.1. The pure warfarin sodium may be isolated by appropriate solvent evaporation technologies, preferably thin or wipe film technology, at temperatures less than about 70° C., and preferably less than about 50° C. Alternatively, the solvent may be evaporated at low temperature until a heavy syrup is obtained, the resulting syrup poured into trays and additional ethanol evaporated in a drying oven at a temperature of less than about 100° C., preferably less than about 70° C. When drying is nearly complete, the solid is ground to a fine powder, preferably passing through a 60 mesh screen and then returned to the oven to complete drying at temperatures less than about 100° C. It has been observed using existing methods that further evaporation of solvent from the syrup results in gel formation. Solidification of the gel may be accomplished only using more severe heating and mechanical treatment, which may result in decomposition of the warfarin sodium.

As shown in the non-limiting example which follows, the following parameters are in the preparation of pure warfarin sodium:

1. Sodium carbonate is preferably used in excess, preferably as a fine powder, in order to obtain a complete reaction at low temperature in a short reaction time. A lower salt to warfarin ratio results in less decomposition but a slower reaction. The preferred ratio of molar equivalents of sodium carbonate to warfarin acid was found to be between about 1.1 to 1.5:1.

2. Sodium carbonate is soluble in water and exhibits poor solubility in absolute ethanol.

However, increasing the water content during the reaction causes a decrease in pH control. Thus, contrary to principles of solubility, by using absolute ethanol, more direct pH control is obtained. Although superior results are obtained in absolute ethanol, other polar solvents may, in principle, be used. Anhydrous solvents are preferred, but use of substantially anhydrous solvents, i.e. solvents containing less than about 10% water, is also contemplated by the invention.

3. High purity warfarin sodium is obtained when the product is precipitated by evaporation of the solvent to dryness at a low temperature, preferably less than about 70° C., and more preferably at less than about 50° C.

4. Maintaining the reaction temperature at between about 20° C. and about 35° C. allows for direct production of a pure product. An increase in temperature leads to a decrease in product quality due to accelerated decomposition at higher temperatures.

5. Inferior results were found with isopropanol, in which a clathrate forms, and methanol. It is critical that the solvent not lead to formation of a clathrate, decomposition or back-reaction. Ethanol at a concentration of greater than 90% is preferred. Such a solvent must be substantially anhydrous (less than about 10% water), and is referred to have as a "stabilizing anhydrous polar solvent." Without limitation, it is believed that such solvents avoid the strong hydrogen bonding that may occur between water molecules and the warfarin backbone impeding crystallization, as is observed in existing methods of preparation. Use of absolute ethanol is most preferred in the preparation in order to achieve reaction in a short period of time and at a low temperature. In addition, the reduced solubility of sodium carbonate in absolute ethanol allows for superior pH control.

6. To complete the drying of warfarin sodium at a temperature less than about 70° C. in a vacuum, it is advantageous to grind the warfarin sodium through a mesh screen before completion of drying in order to accelerate the evaporation of imprisoned solvent in the crystals and completely remove the ethanol.

The invention is best understood to a person skilled in the art upon consideration of the following non-limiting example. It is to be understood that normal variations requiring routine experimentation to optimize specific conditions in any particular setting are within the scope of the invention.

EXAMPLE

Pure warfarin acid (1 kg), sodium carbonate (0.4 to 0.5 kg) and absolute ethanol (5–6 liter) were combined with stirring. The mixture of materials was stirred at a temperature of less than 30° C. for one hour, and then warmed to 30–35° C. and stirred for up to one additional hour. The insoluble salts were removed from the reaction mixture at room temperature by filtration.

The pH of the filtrate was measured and adjusted to a range of from about 7.8 to about 8. 1. The solvent was then removed by evaporation of a temperature of less than 50° C. and under vacuum until a heavy syrup is reached. (About 80 to 90% of ethanol removal.) The heavy syrup was then poured into trays and evaporation continued in a vacuum oven until the solid was dry. The solid was then removed from the vacuum oven, ground to a fine powder through a 60 mesh screen, and returned back into the trays which were placed in the oven to complete the drying process.

This procedure yielded 1.02 kg of warfarin sodium (95%). The warfarin sodium thus obtained passes the British Pharmacopeial test for color clarity, pH, TLC, water and assay.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for producing warfarin sodium comprising the steps of:
    reacting warfarin acid with an excess of a volatilizable base in a polar organic solvent,
    removing insoluble salts, and
    adjusting the pH to a value of from about 7.8 to about 8.1 to provide a solution of pure warfarin sodium,
    wherein the organic polar organic solvent contains less than about 10% water and does not produce a clathrate, cause decomposition or promote back-reaction under the reaction conditions.

2. The method of claim 1, wherein the polar organic solvent is ethanol.

3. The method of claim 2, wherein the ethanol is absolute ethanol.

4. The method of claim 1, wherein the volatilizable base is selected from the group consisting of sodium carbonate and sodium bicarbonate.

5. The method of claim 1, further comprising removing the solvent by evaporation at a temperature of not more than about 70° C.

6. The method of claim 5, wherein the temperature is not more than about 50° C.

7. The method of claim 4, wherein the ratio of molar equivalents of volatilizable base to warfarin acid is from about 1.1:1 to about 1.5:1.

8. The method of claim 1, wherein the reacting step is conducted at a temperature of less than about 50° C.

9. The method of claim 1, wherein the reacting step is conducted at a temperature of less than about 35° C.

10. The method of claim 5, wherein about 80% to about 90% of the solvent is removed by evaporation.

11. The method of to claim 1, further comprising isolating pure warfarin sodium.

12. The method of claim 11, wherein the pure warfarin sodium is isolated by solvent evaporation.

13. The method of claim 11, wherein the isolating is accomplished using thin or wipe film technology.

14. The method of claim 1, wherein the volatilizable base is sodium carbonate.

15. The process according to claim 10, further comprising the steps of:
    removing additional solvent in a vacuum oven at a temperature of less than about 70° C. until a solid forms,
    grinding the solid into a fine powder, and
    removing any remaining solvent in a vacuum oven at a temperature of less than about 70° C.

16. A method for producing warfarin sodium comprising the steps of:
    reacting warfarin acid with sodium carbonate at a temperature of less than about 30° C. in absolute ethanol,
    heating the resulting solution to a temperature of between about 30° C. and about 35° C.,
    removing insoluble salts by filtration at room temperature,
    adjusting the pH to a value of from about 7.8 to about 8.1,
    removing the absolute ethanol by evaporation at a temperature of not more than about 50° C. to form a syrup,
    pouring the syrup into evaporation trays,
    removing additional absolute ethanol in a vacuum at a temperature of less than about 70° C. until a solid forms,
    removing the solid from the vacuum and grinding the solid into a fine powder, and
    removing any remaining solvent in a vacuum at a temperature of less than about 70° C. to produce pure warfarin sodium,
    wherein the ratio of molar equivalents of sodium carbonate to warfarin acid is from about 1.1:1 to about 1.5:1.

17. A method for producing pure warfarin sodium comprising the steps of:
    step for providing pure warfarin acid, a volatilizable base, and a polar organic solvent,
    step for producing crude warfarin sodium from the warfarin acid and the base in the polar organic solvent at ambient temperature,
    step for removing solid impurities from said crude warfarin sodium, and
    step for obtaining a pH in a range of from about 7.8 to about 8.1, to produce a pure warfarin sodium,
    wherein the inorganic base is selected from the group consisting of sodium carbonate and sodium bicarbonate, and
    wherein the polar solvent contains less than about 10% water and does not produce a clathrate, cause decomposition or promote back-reaction under the conditions for producing crude warfarin sodium.

18. The method of claim 17, wherein the solvent is ethanol.

19. The method of claim 18, wherein the ethanol is absolute ethanol.

20. The method of claim 17, wherein the base is selected from the group consisting of sodium carbonate and sodium bicarbonate.

21. The method of claim 17, wherein the base is sodium carbonate.

22. The method of claim 17, further comprising a step for isolating pure warfarin sodium by solvent evaporation.

23. The method of claim 18, further comprising a step for evaporating ethanol from the pure warfarin sodium.

24. The method of claim 23, wherein said step for evaporating ethanol comprises step for converting the pure warfarin sodium preparation to a syrup from which about 80% to about 90% of the ethanol is evaporated, step for converting the syrup to a solid, step for generating a finely divided solid, and step for removing any remaining ethanol.

25. The method of claim 24, wherein the about 80% to about 90% of ethanol is evaporated at a temperature of less than about 50° C.

26. The method of claim 24, wherein said step for converting the syrup to a solid is conducted in a vacuum at a temperature of less than about 70° C.

27. The method of claim 24, wherein said step for removing any remaining ethanol is conducted at a temperature of less than about 70° C.

* * * * *

UNITED STATES PATENT AND TRADEMARK OFFICE
CERTIFICATE OF CORRECTION

PATENT NO. : 6,673,944 B2
DATED : January 6, 2004
INVENTOR(S) : Ashkar et al.

It is certified that error appears in the above-identified patent and that said Letters Patent is hereby corrected as shown below:

Title page,
Item [*] Notice, delete the phrase "by 66" and insert -- by 59 days --

Signed and Sealed this

Tenth Day of May, 2005

JON W. DUDAS
*Director of the United States Patent and Trademark Office*